United States Patent [19]

Tsutsumi et al.

[11] 4,348,415

[45] Sep. 7, 1982

[54] COSMETIC AND EMULSIFIER COMPOSITIONS

[75] Inventors: Hisao Tsutsumi, Miyashiro; Kazumi Hori, Koganei; Junichi Kawano, Sakura, all of Japan

[73] Assignee: Kao Soap Co., Ltd., Tokyo, Japan

[21] Appl. No.: 191,847

[22] Filed: Sep. 29, 1980

[30] Foreign Application Priority Data

Oct. 31, 1979 [JP] Japan .................. 54-139789

[51] Int. Cl.³ .................. A61K 7/00; A61K 47/00; B01F 17/30
[52] U.S. Cl. .................. 424/365; 252/356; 424/70; 424/358
[58] Field of Search .............. 424/70, 238, 358, 365; 260/397.2; 252/356, 351

[56] References Cited

PUBLICATIONS

Hradec, Chem. Abs., vol. 73, 1970, Ab. No. 107112x.
Schering, Chem. Abs., vol. 55, 1961, pp. 6789–6790.
Tiedt, Chem. Abs., vol. 46, 1952, p. 9325d.

*Primary Examiner*—Anna P. Fagelson
*Attorney, Agent, or Firm*—Oblon, Fisher, Spivak, McClelland & Maier

[57] ABSTRACT

A cosmetic composition comprising a cosmetic oil component, water and a specific emulsifier are disclosed. The specific emulsifier comprises
 a branched fatty acid cholesterol ester of the formula (I)

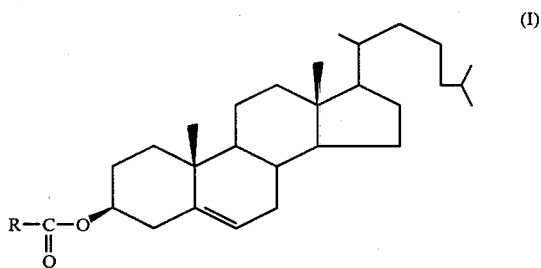

where R is a saturated aliphatic hydrocarbon group having a total of 11 to 23 carbon atoms and including at least one alkyl substituent group attached on the main chain inbetween the carboxyl-bonding position and the center of the main chain, and
 cholesterol;
 wherein said branched fatty acid cholesterol ester and said cholesterol are in a weight ratio of 90:10 to 10:90.

20 Claims, No Drawings

COSMETIC AND EMULSIFIER COMPOSITIONS

BACKGROUND OF THE INVENTION

1. Field of the Invention

The present invention relates to a novel cosmetic composition and, particularly, to an emulsion type cosmetic composition.

2. Description of the Prior Art

Emulsion type cosmetics such as creams or skin lotions, are classified into two types, namely an oil in water (O/W) type emulsion wherein an oil component as the cosmetic base material is dispersed in water with use of an emulsifier and a water in oil (W/O) type emulsion wherein water is dispersed in the oil component.

As emulsifiers for stabilizing such emulsion systems, there have mainly been used non-ionic surface active agents such as polyoxyethylene alkyl ether, an oxyethylene oxypropylene block copolymer, a sorbitan fatty acid ester, and a polyoxyethylene sorbitan fatty acid ester. However, these emulsifiers cause irritation to the skin and they are accordingly not necessarily satisfactory.

On the other hand, it is known that cholesterol having a unique structure with a hydroxyl group at the C-3 position and a double bond at the C-5 and C-6 positions, exhibits surface activity. Cholesterol is widely distributed in nature and, especially in the animal body, it is distributed in almost all systems not to mention epithelial fat, and it plays an important role in physiological processes. Further, cholesterol has a mild penetration property and an activity to keep the skin surface in a moist condition, and it gives little irritation to the skin. Because of these outstanding characteristics suitable for a material for cosmetics, it is used for the production of cosmetics.

There have recently been studies on the reformation of cholesterol in an attempt to obtain a derivative useful as a material for cosmetics. For instance, a technique is reported wherein an alkylene oxide such as ethylene oxide or propylene oxide, is added to cholesterol to improve the hydrophilic property and the cholesterol derivative thus produced are used as an emulsifier for cosmetics (Japanese Patent Publication No. 28501 of 1975).

However, most of the above mentioned cholesterol derivatives have a high melting point and are normally solid at room temperature. Accordingly, it is necessary to take special measures when they are used, and in some cases, the amount of use and the area for application is restricted.

A need therefore continues to exist for emulsifiers suitable for use in cosmetics which are liquid at room temperature and give little irritation to the skin.

SUMMARY OF THE INVENTION

Accordingly, one object of the invention is to provide an emulsifier suitable for use in cosmetic compositions which is liquid at room temperature and gives little irritation to the skin.

Another object of the invention is to provide an emulsifier capable of giving an extremely stable emulsion.

A further object of the invention is to provide cosmetic compositions containing such an emulsifier.

Briefly, these objects and other objects of the invention as hereinafter will become more readily apparent can be attained by providing an emulsifier comprising: a branched fatty acid cholesterol ester of the formula (I):

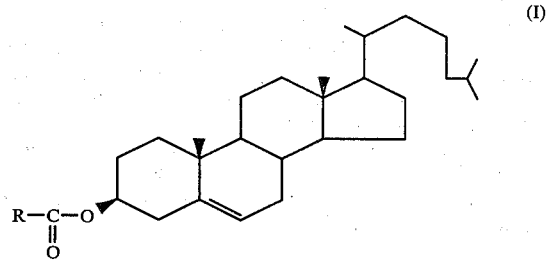

where, R is a saturated aliphatic hydrocarbon group having a total of 11 to 23 carbon atoms and including at least one alkyl substituent attached on the main chain inbetween the carboxyl-bonding position and the center of the main chain; and
cholesterol;
wherein the branched fatty acid cholesterol ester and cholesterol are in a weight ratio of 90:10 to 10:90.

DETAILED DESCRIPTION OF THE PREFERRED EMBODIMENTS

The cholesterol derivative to be used in the present invention is a branched fatty acid cholesterol ester represented by the formula (I):

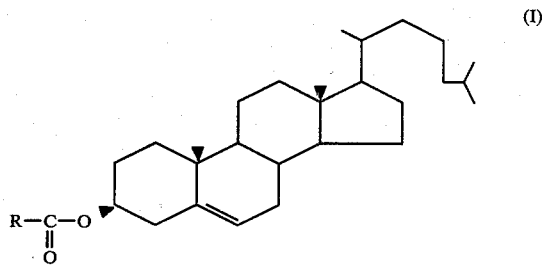

where, R is a saturated aliphatic hydrocarbon group having a total of 11 to 23 carbon atoms, and including at least one alkyl substituent group attached on the main chain inbetween the carboxyl bonding position and the center of the main chain.

Such branched fatty acid cholesterol esters are novel compounds, and they may be prepared by standard methods normally used for the production of an ester from a branched fatty acid or its derivative and cholesterol. A branched fatty acid and cholesterol may be reacted directly for esterification, or either one of them may firstly be converted to a reactive derivative before the esterification. Preparation of these compounds is disclosed in copending U.S. Application Ser. No. 191,825 filed concurrently herewith, the disclosure of which is incorporated herein by reference.

As a branched fatty acid (RCOOH) to be used as the starting material for the production of the branched fatty acid cholesterol ester, those having 12 to 24 carbon atoms (11 to 23 carbon atoms in R) are useful. However, those having 14 to 20 carbon atoms (13 to 19 carbon atoms in R) are preferred, and the one having 18 carbon atoms is most preferred. If a branched fatty acid having less than 12 carbon atoms is used, the branched fatty acid cholesterol ester thereby obtained will not have a sufficient oleophilic property. On the other hand, if the one having more than 24 carbon atoms is used, the product will not have a sufficient hydrophilic property.

The branched fatty acid must have at least one alkyl group attached on the main chain at a position inbetween the carboxyl-attaching position and the center of the main chain. Such a saturated branched fatty acid is readily available from the petrochemical industry or the oil and fat chemical industry.

As an example of such a branched fatty acid available from the petrochemical industry, there is a branched fatty acid having a side chain at the $\alpha$-position and represented by the following formula (II)

where, each of $R_1$ and $R_2$ is a straight or branched chain saturated aliphatic hydrocarbon, and the total number of carbon atoms in $R_1$ and $R_2$ is 12 to 18.

The branched fatty acid having a side chain at the $\alpha$-position and represented by the above formula (II) may be prepared, for instance, by subjecting a straight or branched chain aldehyde having 7 to 10 carbon atoms to an aldol condensation and then subjecting the $\alpha$-branched unsaturated aldehyde thus obtained to hydrogenation and oxidation to obtain a branched saturated fatty acid.

Preferred representatives of the saturated branched fatty acid having a side chain at the $\alpha$-position, are 5,7,7-trimethyl-2-(1,3,3-trimethylbutyl)-octanoic acid, 2-heptyl undecanoic acid, and 2-hexyl decanoic acid.

As an example of a saturated branched fatty acid available from the material of the oil and fat chemical industry, there is a fatty acid having a methyl branched chain represented by the following formula (III):

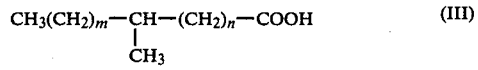

where the total of m+n is 14, and the distribution is centered about m=n=7.

Such a methyl branched chain fatty acid is obtainable, for instance, as a by-product in the production of a dimer of oleic acid (e.g. J. Amer. Oil Chem. Soc., 51,522 (1974)) and is referred to in this specification as "methyl branched isostearic acid". The methyl branched isostearic acid is sold, for instance, in the form of its isopropyl ester (U.S. Emery Industry Inc. etc).

The cholesterol to be used in the present invention is not restricted to that prepared by any particular method, but it may be extracted or extracted and refined from natural substances, for instance, from dried cow's brain or marrow. Further, the cholesterol may partly or wholly be substituted by a substance containing cholesterol, such as hydrous lanolin. In this case, however, it is necessary to calculate the amount to be used on the basis of the cholesterol content.

The emulsifier to be used in the present invention is a combination of the branched fatty acid cholesterol ester and cholesterol in a weight ratio of 90:10 to 10:90, preferably 70:30 to 20:80.

As the cosmetic oil component, there may be mentioned a hydrocarbon such as liquid paraffin, vaseline, paraffin, ceresine or squalane; a natural wax such as bees' wax, whale wax, carnauba wax, hydrous lanolin, or jojoba oil; a plant oil such as olive oil, camellia oil, or cotton oil; a higher alcohol, a higher fatty acid, various esters obtainable from a higher fatty acid and a higher alcohol, and silicone oil. If a substance containing cholesterol, such as hydrous lanolin, is used as the oil component, the amount of the cholesterol to be added may be reduced or omitted, as mentioned above.

The cosmetic composition of the present invention may be prepared by a usual method in wich 0.1 to 30% by weight, preferably 0.5 to 5% by weight, of an emulsifier obtained by mixing the branched fatty acid cholesterol ester and cholesterol in the predetermined proportions, 0.1 to 90% by weight, preferably 1 to 50% by weight, of the cosmetic oil component, and 1 to 99% by weight, preferably 20 to 90% by weight, of water, are mixed and emulsified.

Further, it is possible to add various components which are normally used to improve the quality of cosmetics, such as a moisture retaining agent, e.g. glycerin, propylene glycol, 1,3-butylene glycol, sodium pyrrolidonecarboxylate; a viscosity increasing agent e.g. polyvinylalcohol, carboxy vinyl polymer, carboxy methyl cellulose, polyvinylpyrrolidone, hydroxy ethyl cellulose, methyl cellulose, gelatin, carrageenan, or tragacanth gum; an antiseptic agent e.g. methyl parahydroxybenzoate, ethyl parahydroxybenzoate, propyl parahydroxybenzoate, butyl parahydroxybenzoate, benzoic acid, sodium benzoate, or phenoxyethanol; or various medicinal agents, and perfumes.

Further, conventional emulsifiers such as a non-ionic surface active agent e.g. a polyoxyethylene alkyl ether, a polyoxyethylene fatty acid ester, a polyoxyethylene sorbitan fatty acid ester, a polyoxyethylene hydrogenated castor oil, a sucrose fatty acid ester, a glycerin fatty acid ester, a sorbitan fatty acid ester; and an anionic surface active agent e.g. an alkyl phosphoric acid ester, an alkyl sulfate ester, a soap, a polyoxyethylene alkyl phosphate acid ester or a polyoxyethylene alkyl sulfate may also be used to an extent not to impair the effectiveness of the present invention.

Furthermore, in the preparation of a W/O type cosmetic composition, lecithin, an inorganic salt such as magnesium sulfate, potassium sulfate, aluminum sulfate, sodium nitrate or calcium chloride, and a multi-valent metal salt of a fatty acid such as aluminum monostearate, aluminum distearate or calcium monostearate, are useful for stabilizing the W/O type emulsion, and may preferably be used together with the emulsifier of the present invention.

In the case where a O/W type cosmetic composition is prepared, it is useful and preferable to combine the emulsifier of the present invention with lecithin or an anionic surface active agent such as alkyl sulfuric acid ester, alkyl phosphoric acid ester or an alkali metal salt of a fatty acid.

The general composition of the cosmetic composition of the present invention is as follows:

| Components | Range (% by weight) | Preferred range (% by weight) |
| --- | --- | --- |
| Emulsifier (a mixture of a branched fatty acid cholesterol ester and cholesterol) | 0.1~30 | 0.3~5 |
| Cosmetic oil component | 0.1~90 | 1~50 |
| Water | 1~99 | 20~90 |

-continued

| Components | Range (% by weight) | Preferred range (% by weight) |
|---|---|---|
| Moisture retaining agent | 0~20 | 0~10 |
| Viscosity increasing agent | 0~5 | 0~2 |
| Antiseptic agent | 0~2 | 0~0.5 |
| Other emulsifier | 0~10 | 0~5 |
| Medicinal component | 0~2 | 0~0.5 |
| Perfume | 0~2 | 0~0.5 |
| Stabilizer | 0~10 | 0~5 |

The cosmetic composition of the present invention is an emulsion type cosmetic composition adapted to keep the skin from drying, protect the skin from outside irritation, prevent roughening of the skin, and to maintain the skin fresh, and may take any form, for instance, it may be in the form of a vanishing cream, a hand cream, a cleansing cream, a foundation cream, a hair cream, a cold cream, a milky lotion or a lotion.

Having generally described this invention, a further understanding can be obtained by reference to certain specific examples which are provided herein for purposes of illustration only and are not intended to be limiting unless otherwise specified.

Preparatory Example 1

Into a reactor having a capacity of 2 liters and equipped with a thermometer, a reflux condenser, a dropping funnel, and a stirrer means, 568 g (2.0 moles) of isostearic acid (5,7,7-trimethyl-2-(1,3,3-trimethylbutyl)octanoic acid, made by Nissan Chemical Industries Co., Ltd.) were fed. While stirring and supplying nitrogen gas, 286 g (2.4 moles) of thionylchloride were added dropwise from the dropping funnel at room temperature. As the dropwise addition of thionyl chloride proceeded, the reaction mixture underwent a colour change from colourless, light yellow to dark brown, and at the same time, gas generation was observed. During the dropwise addition of the thionyl chloride, the temperature of the reaction mixture was maintained at room temperature. After the dropwise addition of thionyl chloride for about 3 hours, the reaction mixture was further held at 60° to 70° C. for about 3 hours by an oil bath. After confirming that there was no more generation of gas, low boiling point substances were removed under a reduced pressure, and then a distillation under a reduced pressure was carried out. 588 g of a distillate at 112° to 120° C./0.1 to 0.3 mmHg was obtained (97% yield). This was confirmed to be 5,7,7-trimethyl-2-(1,3,3-trimethyllbutyl)octanoic chloride.

IR spectrum (liquid film method) 2970, 2920, 2875, 1795 (C=O stretching vibration), 1480, 1390, 1370, 1260, 1210, 995, 930, 790, 710, 600 cm$^{-1}$ H$^1$-NMR spectrum (CCl$_4$ solvent): δ 0.9 (s, 24H, C$\underline{H}_3$-) 1.1 to 2.0 (m, 10H, -C$\underline{H}_2$- and

2.5 (m, 1H, >C$\underline{H}$COCl)

Preparatory Example 2

Into a reactor having a capacity of 2 liters and equipped with the same devices as employed in Preparatory Example 1, 571 g (2.0 moles) of isostearic acid (2-heptyl undecanoic acid made by Mitsubishi Chemical Industries Ltd.) were fed, and while stirring and supplying nitrogen gas, 286 g (2.4 moles) of thionyl chloride were added dropwise from the dropping funnel at room temperature. As the dropwise addition of thionyl chloride proceeded, the reaction mixture underwent the same colour change as observed in Preparatory Example 1. During the dropwise addition of thionyl chloride, the temperature of the reaction mixture was maintained at room temperature. After the dropwise addition of thionyl chloride for about 3 hours, the reaction mixture was further held at 60° to 70° C. for about 3 hours. After confirming that there was no more generation of gas, lower boiling point substances were removed under a reduced pressure, and then a distillation under a reduced pressure was carried out, whereupon 549 g of a distillate at 145° to 151° C./0.25 to 0.3 mmHg were obtained (91% yield). This was confirmed to be 2-heptyl undecanoic chloride.

IR spectrum (liquid film) 2960, 2925, 2850, 1790 (C=O stretching vibration), 1460, 1380, 900, 830, 720, 700, 600 cm$^{-1}$ H$^1$-NMR (CCl$_4$ solvent): δ 0.83 (t, 6H, C$\underline{H}_3$CH$_2$-) 1.0 to 2.0 (m, 28H, -C$\underline{H}_2$-) 2.65 (m, 1H, >C$\underline{H}$COCl)

Preparatory Example 3

With use of a reactor having a capacity of 3 liters and equipped with the same devices as employed in Preparatory Example 1, 569 g (2.0 moles) of isostearic acid (Emery 875 isostearic acid made by US Emery Industry Inc. and being a methyl branched fatty acid represented by the formula (III)) were reacted with 520 g (4.4 moles) of thionyl chloride in the same manner as in Preparatory Example 1. After the reaction, lower boiling point substances were removed and about 230 g of a low boiling material which was considered to be thionyl chloride, were recovered. Then, a distillation under a reduced pressure was carried out, whereupon 454 g of a distillate at 153° to 170° C./1.0 to 3.0 mmHg were obtained (75% yield). This was confirmed to be methyl branched isostearic chloride.

IR spectrum (liquid film method) 2950, 2920, 2850, 1800 (C=O stretching vibration), 1460, 1400, 1380, 950, 720, 680, 590 cm$^{-1}$ H$^1$-NMR spectrum (CCl$_4$): δ 0.6 to 1.0 (m, C$\underline{H}_3$CH$_2$- and

1.0 to 1.5 (m, -C$\underline{H}_2$-) 1.5 to 2.0

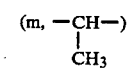

2.77 (t, -C$\underline{H}_2$COCl)

Preparatory Example 4

Into a reactor having a capacity of 3 liters and equipped with a thermometer, a dropping funnel, a reflux condenser and a stirrer means, 281 g (0.73 mole) of cholesterol, 1100 ml of benzene and 65 g (0.82 mole) of pyridine were added in this order. While stirring and supplying nitrogen gas, the reaction mixture was heated to 50° C. by an oil bath, and then 212 g (0.70 mole) of 5,7,7-trimethyl 2-(1,3,3-trimethylbutyl)octanoic chloride obtained by Preparatory Example 1 were added dropwise from the dropping funnel at a temperature of about 50° C. in about 3 hours. After the completion of the dropwise addition, the reaction mixture was further heated at 60° to 80° C. and stirred for about 5 hours. The IR spectrum of the reaction product at this stage indicated that there still remained a small amount of the acid chloride. White precipitates consisting of pyridine chloride in the reaction product were removed by filtration, and after removing the solvent under a reduced pressure, the filtrate thus obtained was heated under a reduced pressure of 0.5 to 0.7 mmHg at a temperature of 190° to 200° C. for about 5 hours. After this treatment, the IR spectrum showed that the acid chloride had disappeared completely. The product thus obtained was then vigorously mixed with benzene (1000 ml) and a diluted hydrochloric acid (1000 ml) and thereafter the benzene layer was separated. The benzene layer was dried with sodium sulfate anhydride and the benzene was removed under a reduced pressure, whereupon 465 g of 5,7,7-trimethyl-2-(1,3,3-trimethylbutyl)octanoic acid cholesterol ester were obtained as a viscous, light yellow, liquid (96% yield).

IR spectrum (liquid film method) 2950, 2900, 2870, 1720 (C=0 stretching vibration), 1470, 1380, 1360, 1240, 1220, 1160, 1030, 1010 cm$^{-1}$ H$^1$-NMR spectrum (CCl$_4$ solvent): δ 0.65 (s, 3H, steroid structure C-18 methyl group) 0.85 (d, 6H, steroid structure side chain C-26, C-27 methyl group) 0.87 (s, 24H, fatty acid side chain methyl group) 1.0 to 2.5 (m) 4.40

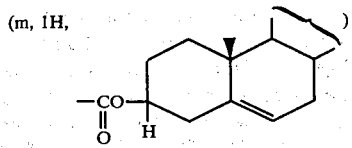

5.25 (m, 1H, steroid structure C-6 olefin proton)

| Acid value | 0.8 (Calculated value 0) |
|---|---|
| Saponification value | 85.8 (Calculated value 86.0) |
| Hydroxyl value | 0.7 (Calculated value 0) |
| Iodine value | 41.0 (Calculated value 39.0) |

Preparatory Example 5

Into a reactor having a capacity of 3 liters and equipped with the same devices as employed in Preparatory Example 4, 271 g (0.70 mole) of cholesterol, 1500 ml of benzene, and 65 g (0.82 mole) of pyridine were introduced in this order. While stirring and supplying nitrogen gas, 212 g (0.70 mole) of 2-heptyl undecanoic chloride obtained by Preparatory Example 2 were added dropwise from the dropping funnel. During this operation, the temperature of the reaction mixture was maintained at 25° to 30° C. After the completion of the dropwise addition of the acid chloride in about 2 hours, the reaction mixture was held at 60° to 80° C. for about 6 hours in an oil bath. The IR spectrum at this stage showed that there still remained a small amount of the acid chloride. The reaction mixture was treated in the same manner as in Preparatory Example 4 and then subjected to a heat treatment in the same manner, whereupon the reaction mixture was confirmed to contain no acid chloride by means of the IR spectrum. 456 g of 2-heptyl undecanoic acid cholesterol ester were obtained as a light yellow liquid having a low viscosity (94% yield).

IR spectrum (Liquid film): 2950, 2930, 2850, 1730 (C=0 stretching vibration), 1465, 1380, 1365, 1260, 1160, 1050 cm$^{-1}$ H$^1$-NMR spectrum (CCl$_4$ solvent): δ 0.68 (s, 3H, steroid structure C-18 methyl group) 0.80 (d, 6H, steroid structure side chain C-26, C-27 methyl group) 1.00 (s, 3H, steroid structure C-19 methyl group) 0.8 to 1.1 (m, 6H, branched fatty acid side chain CH$_3$CH$_2$- 1.1 to 2.4 (m) 4.4

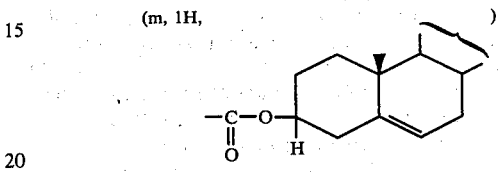

5.25 (m, 1H, steroid structure C-6 olefin proton)

| Acid value | 0.7 (Calculated value 0) |
|---|---|
| Saponification value | 86.5 (Calculated value 86.0) |
| Hydroxyl value | 0.5 (Calculated value 0) |
| Iodine value | 40.0 (Calculated value 39.0) |

Preparatory Example 6

Into a reactor having a capacity of 3 liters and equipped with the same devices as employed in Preparatory Example 4, 281 g (0.73 mole) of cholesterol, 1500 ml of benzene and 100 g (1.27 mole) of pyridine were introduced in this order. While stirring, keeping the temperature at 25° to 30° C. and supplying nitrogen gas, 212 g (0.70 mole) of the methyl branched isostearic chloride obtained by Preparatory Example 3 were added dropwise from the dropping funnel. After the completion of the dropwise addition, the reaction mixture was heated at 50° C. for 3 hours and was further held at 70° to 80° C. for about 8 hours. By this heat treatment, the esterification reaction proceeded completely, and it was confirmed by the IR spectrum that the reaction mixture contained no acid chloride. The reaction mixture was treated in the same manner as in Preparatory Example 4 and 460 g of methyl branched isostearic acid cholesterol ester were obtained as a viscous, light yellow liquid (94% yield).

IR spectrum (liquid film): 2950, 2920, 2850, 1730 (C=0 stretching vibration), 1460, 1370, 1160, 1000 cm$^{-1}$ H$^1$-NMR spectrum (CCl$_4$ solvent): δ 0.70 (s, 3H, steroid structure C-18 methyl group) 0.80 (d, 6H, steroid structure side chain C-26, C-27 methyl group) 1.00 (s, 3H, steroid structure C-19 methyl group) 0.80 to 1.0

(m, 6H, branched fatty acid CH$_3$CH$_2$— and

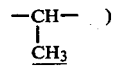

1.0 to 2.0 (m) 2.2 (t, 2H, -CH$_2$-CH$_2$-COO-) 4.4

(m, 1H, 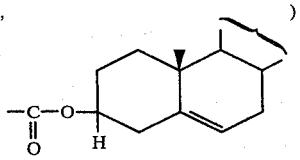 )

5.25 (m, 1H, steroid structure C-6 olefin proton)

| | |
|---|---|
| Acid value | 0.8 (Calculated value 0) |
| Saponification value | 84.8 (Calculated value 86.0) |
| Hydroxyl value | 0.7 (Calculated value 0) |
| Iodine value | 41.4 (Calculated value 39.0) |

EXAMPLE 1

Emulsion tests were conducted with use of the emulsifiers of the present invention and comparative products, wherein the emulsifying powers were compared. The emulsion tests were conducted in the following manner: 0.3 g of the composition to be tested was added to 9.7 g of vaseline, heated and stirred to obtain a homogeneous mixture. The mixture was then cooled and ion-exchanged water was gradually added, while stirring, thereby emulsifying the mixture. In this operation, a homogeneous W/O cream was formed at the initial stage. However, when the amount of water added exceeded a certain point, there appeared a phase separation. The maximum amount (g) of added water, beyond which the phase separation occurs, was determined with respect to each composition tested, and the emulsifying power was calculated in accordance with the following formula:

$$\text{Emulsifying power} = \frac{\text{Maximum amount of added water (g)}}{10 \text{ (g)}} \times 100$$

The results are shown in Table 1.

TABLE 1

| Composition tested (weight ratio) | Emulsifying power |
|---|---|
| Present Invention | |
| Methyl branched isostearic acid cholesterol ester/cholesterol (84/16) | 280 |
| Same as above (50/50) | 640 |
| Same as above (33/67) | 260 |
| 2-heptyl undecanoic acid cholesterol ester/cholesterol (50/50) | 380 |
| 5,7,7-trimethyl-2-(1,3,3-trimethylbutyl) octanoic acid cholesterol ester/cholesterol (50/50) | 290 |
| Comparative Products | |
| Methyl branched isostearic acid cholesterol ester | 65 |
| 2-heptyl undecanoic acid cholesterol ester | 40 |
| 5,5,7-trimethyl-2(1,3,3-trimethylbutyl) octanoic acid cholesterol ester | 25 |
| Stearic acid cholesterol ester/cholesterol (50/50) | 100 |
| Cholesterol | 50 |
| Hydrous lanolin | 90 |

From the above test results, it is apparent that the emulsifying power is remarkably improved by combining the branched fatty acid cholesterol ester of the formula (I) with cholesterol, as compared with the emulsifying power of each individual component or hydrous lanolin which was used for the same purpose.

EXAMPLE 2

Animal tests were carried out with respect to the branched fatty acid cholesterol esters to be used in the present invention and comparative products to investigate irritation to the skin. The tests were conducted in the following manner: White guinea pigs were hair cut at their backs by an electrical hair cutter 7 hours prior to the tests. 12 hair cut guinea pigs having a healthy skin, were fixed on a fixing board. A proper amount of the substance to be tested was applied to the exposed skin on the back of each guinea pig, in the shape of a disc having a diameter of 2 cm, and it is left as it is. This operation was repeated once a day for four days. Evaluation was made immediately before every application of the substance to be tested and 24 hours after the final application on the basis of the following standards:

| Standards for evaluation: | Evaluated Value |
|---|---|
| (Whether or not there appears erythema) | |
| No change | 0.0 |
| Slight erythema observed | 0.5 |
| Moderate erythema observed | 1.0 |
| Strong erythema observed | 2.0 |
| (Whether or not there appears edema) | |
| No change | 0.0 |
| Slight edema observed | 0.5 |
| Moderate edema observed | 1.0 |
| Strong edema observed | 2.0 |

The erythema appearance and edema were evaluated independently of each other, and both evaluations were added up for point evaluations.

The results are shown in Table 2.

TABLE 2

| | Evaluated Points | | | | |
|---|---|---|---|---|---|
| Substances tested | One day after | Two days after | Three days after | Four days after | Average |
| Present Invention | | | | | |
| Methyl branched isostearic acid cholesterol ester | 0.0 | 0.0 | 0.0 | 0.0 | 0.0 |
| 2-heptyl undecanoic acid cholesterol ester | 0.0 | 0.0 | 0.0 | 0.0 | 0.0 |
| 5,7,7-trimethyl-2-(1,3,3-trimethyl butyl)octanoic acid cholesterol | 0.0 | 0.0 | 0.0 | 0.0 | 0.0 |
| Comparative Product | | | | | |
| Oleic acid cholesterol ester | 0.6 | 0.2 | 0.6 | 1.0 | 0.6 |

It was confirmed by the results of these tests that the branched fatty acid cholesterol esters to be used in the present invention, do not irritate the skin and that they are extremely useful as an emulsifier for cosmetics.

EXAMPLE 3

An O/W emulsification of olive oil was investigated with use of the emulsifiers of the present invention and comparative products. The emulsification tests were conducted in the following manner: 45 parts of olive oil, 2 parts of the composition to be tested, and 53 parts of ion-exchanged water were heated to 70° C. and stirred. After cooling the mixture to room temperature, the emulsion was put in a test tube and kept at 25° C. The evaluation of the emulsion was made with respect to the state immediately after its preparation and the separation state one day after. The standards for the evaluation were as follows:

Emulsified states
 A: homogeneous O/W emulsion
 B: coarse particle emulsion
 C: immediately separated upon being left to stand still Separation states
 —: no separation observed
 +: coagulated phase by creaming observed
 ++: coagulated phase and coalesced phase observed
 +++: separation into a water phase and an oil phase The results are shown in Table 3.

|  | Composition of the compositions tested | (wt %) | | | Emulsion types | Emulsified states | Separation states |
|---|---|---|---|---|---|---|---|
| Present invention | Methyl branched isostearic acid cholesterol ester | | Cholesterol | Lecithin | | | |
| | 5 | | 5 | 90 | O/W | A | — |
| | 10 | | 10 | 80 | O/W | A | — |
| | 20 | | 20 | 60 | O/W | A | — |
| | 30 | | 30 | 40 | W/O | A | — |
| | 40 | | 40 | 20 | W/O | A | — |
| | 50 | | 50 | 0 | W/O | A | — |
| Comparative products | Stearic acid cholesterol ester | | Cholesterol | Lecithin | | | |
| | 5 | | 5 | 90 | O/W | C | ++ |
| | 10 | | 10 | 80 | O/W | C | ++ |
| | Hydrous lanolin | | Cholesterol | Lecithin | | | |
| | 5 | | 5 | 90 | O/W | C | +++ |
| | 10 | | 10 | 80 | O/W | C | +++ |

From the results of these tests, it is apparent that a combination of the branched fatty acid cholesterol ester and cholesterol according to the present invention, exhibits an emulsifying power superior to other combinations of a conventional emulsifier and cholesterol.

EXAMPLE 4 SKIN CREAM (W/O TYPE)

(Composition)

| 1. Methyl branched isostearic acid cholesterol ester | 1.0 % by weight |
|---|---|
| 2. Cholesterol | 1.0 |
| 3. Lecithin | 0.5 |
| 4. Vaseline | 15.0 |
| 5. Hexadecyl-2-ethyl hexanoate | 10.0 |
| 6. Aluminum monostearate | 0.1 |
| 7. Magnesium sulfate | 1.0 |
| 8. Sodium benzote | 0.3 |
| 9. Ion-exchanged water | Balance |
| 10. Perfume | 0.1 |

(Method for preparation)

Components 1 to 6 were mixed and heated to 70° C. Components 7 to 9 were heated and mixed at 75° C., and this mixture was added to the mixture of components 1 to 6 and emulsified. After cooling, conponent 10 was added to obtain a homogeneous emulsion.

The skin cream thus obtained was a W/O type cream having a luster, being stable for a long period of time, and giving a good feeling upon application to the skin with a good compatibility to the skin without giving a sticky or oily feeling.

EXAMPLE 5 MILKY LOTION (O/W TYPE)

(Composition)

| 1. 2-Heptyl undecanoic acid cholesterol ester | 0.2% by weight |
|---|---|
| 2. Cholesterol | 0.2 |
| 3. Lecithin | 2.0 |
| 4. Liquid paraffin | 8.0 |
| 5. Cetostearyl alcohol | 1.0 |
| 6. Methyl para-hydroxy benzoate | 0.1 |
| 7. Ion-exchanged water | Balance |
| 8. Perfume | 0.2 |

(Method for preparation)

Components 1 to 5 were heated to 75° C. and mixed. Components 6 and 7 were heated to 75° C. and mixed, and this mixture was added to the mixture of components 1 to 5 while stirring, thereby emulsifying the combined mixture. After cooling, component 8 was added to obtain a homogeneous emulsion.

The emulsion thus obtained was an O/W type milky lotion having fine texture, being stable for a long period of time, and giving a good feeling with a good compatibility to the skin without giving a sticky or oily feeling.

EXAMPLE 6 CLEANSING CREAM (W/O TYPE)

(Composition)

| 1. Methyl branched isoarachic acid cholesterol ester | 1.5 % by weight |
|---|---|
| 2. Cholesterol | 0.7 |
| 3. Vaseline | 5.0 |
| 4. Liquid paraffin | 45.0 |
| 5. Methyl polysiloxane | 5.0 |
| 6. Ceresine wax | 3.0 |
| 7. Polyethylene glycol 4000 | 10.0 |
| 8. Sorbitol | 8.0 |
| 9. Ethyl para-hydroxy benzoate | 0.2 |
| 10. Ion-exchanged water | Balance |
| 11. Perfume | 0.2 |

(Method for preparation)

Components 1 to 6 were mixed and heated to 75° C. Components 7 to 10 were mixed and heated to 75° C. The mixture of components 7 to 10 was added to the mixture of components 1 to 6 while stirring, thereby emulsifying the combined mixture. After cooling, component 11 was added to obtain a homogeneous emulsion.

The cleansing cream thus obtained was a W/O type cream having a luster, being stable for a long period of time and giving a good feeling when applied to the skin, with a good compatibility to the skin.

EXAMPLE 7 FOUNDATION CREAM (O/W TYPE)

(Composition)

| | |
|---|---|
| 1. Methyl branched isopalmitic acid cholesterol ester | 2.0% by weight |
| 2. Cholesterol | 1.0 |
| 3. Sodium cetyl sulfate | 1.0 |
| 4. Bentonite | 8.0 |
| 5. Talc | 6.0 |
| 6. Titanium oxide | 4.0 |
| 7. Red iron oxide | 0.5 |
| 8. Stearic acid | 5.0 |
| 9. Isopropylmyristate | 3.0 |
| 10. Butyl para-hydroxy benzoate | 0.2 |
| 11. Glycerin | 5.0 |
| 12. Propylene glycol | 3.0 |
| 13. Methyl para-hydroxy benzoate | 0.2 |
| 14. Ion-exchanged water | Balance |
| 15. Perfume | 0.2 |

(Method for preparation)

Components 1, 2 and 8 to 10 were heated and mixed at 70° C., and mixed thereto while stirring was a mixture of components 3 and 11 to 14 heated at 70° C., thereby emulsifying the combined mixture. To the mixture kept at 70° C., components 4 to 7 were added, and stirred and mixed again. After cooling, component 15 was added to obtain a homogeneous emulsion.

The foundation cream thus obtained had a luster and was an O/W type cream having fine texture, being stable for a long period of time and giving a good feeling upon application with a good compatibility to the skin.

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. A cosmetic composition which comprises 0.1 to 30% by weight of an emulsifier, a cosmetic oil component and water; wherein said emulsifier consists essentially of a branched fatty acid cholesterol ester of the formula (I):

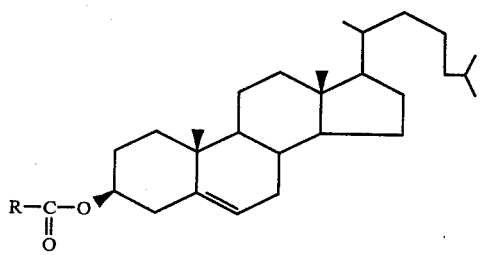

where R is a saturated aliphatic hydrocarbon group having a total of 11 to 23 carbon atoms and including at least one alkyl substituent group attached on the main chain inbetween the carboxyl-bonding position and the center of the main chain, and cholesterol:

wherein said branched fatty acid cholesterol ester and said cholesterol are in a weight ratio of 90:10 to 10:90.

2. The cosmetic composition as claimed in claim 1, wherein R in the formula (I) is a hydrocarbon group having a total of 13 to 19 carbon atoms.

3. The composition as claimed in claim 2, wherein R in the formula (I) is a hydrocarbon group represented by the formula (III)

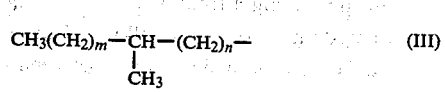

where the total of $m+n$ is 14, and the distribution is centered about $m=n=7$.

4. The cosmetic composition as claimed in claim 2, wherein R in the formula (I) is a hydrocarbon group represented by the formula (II)

where each of $R_1$ and $R_2$ is a straight or branched chain saturated aliphatic hydrocarbon group and the total number of carbon atoms in $R_1$ and $R_2$ is 12 to 18.

5. The cosmetic composition as claimed in claim 4, wherein the total number of carbon atoms in $R_1$ and $R_2$ in the formula (II) is 16.

6. The cosmetic composition as claimed in claim 4 or 5, wherein $R_1$ and $R_2$ in the formula (II) are each a branched saturated aliphatic hydrocarbon group.

7. The cosmetic composition as claimed in claim 1, wherein R is a 5,7,7-trimethyl-2-(1,3,3-trimethylbutyl)-octyl group.

8. The cosmetic composition as claimed in claim 4 or 5, wherein $R_1$ and $R_2$ in the formula (II) are each a straight chain saturated aliphatic hydrocarbon group.

9. The cosmetic composition as claimed in claim 1, wherein R is a 2-heptyl undecyl group.

10. The cosmetic composition as claimed in claim 1, which comprises 0.1 to 30% by weight of a total of the branched fatty acid cholesterol ester and cholesterol, 0.1 to 90% by weight of the cosmetic oil component and 1 to 99% by weight of water.

11. The cosmetic composition as claimed in claim 10, which comprises 0.3 to 5% by weight of a total of the branched fatty acid cholesterol ester and cholesterol, 1 to 50% by weight of the cosmetic oil component, and 20 to 90% by weight of water.

12. An emulsifier composition consisting essentially of:

a branched fatty acid cholesterol ester of the formula (I)

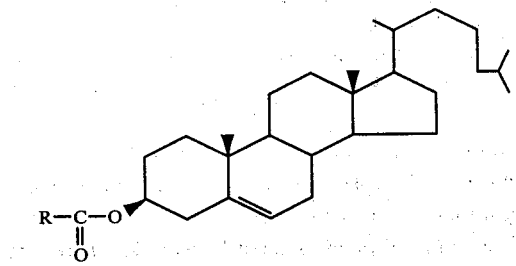

$$R-\underset{\underset{O}{\|}}{C}-O \text{[steroid]} \quad (I)$$

where R is a saturated aliphatic hydrocarbon group having a total of 11 to 23 carbon atoms and including at least one alkyl substituent group attached on the main chain inbetween the carboxyl-bonding position and the center of the main chain, and cholesterol;

wherein said branched fatty acid cholesterol ester and said cholesterol are in a weight ratio of 90:10 to 10:90.

13. The emulsifier composition as claimed in claim 12, wherein R in the formula (I) is a hydrocarbon group having a total of 13 to 19 carbon atoms.

14. The emulsifier composition as claimed in claim 13, wherein R in the formula (I) is a hydrocarbon group represented by the formula (III)

$$CH_3(CH_2)_m-\underset{\underset{CH_3}{\|}}{CH}-(CH_2)_m- \quad (III)$$

where the total of $m+m$ is 14, and the distribution is centered about $m=n=7$.

15. The emulsifier composition as claimed in claim 13, wherein R in the formula (I) is a hydrocarbon group represented by the formula (II)

$$R_1-\underset{\underset{R_2}{\|}}{CH}- \quad (II)$$

where each of $R_1$ and $R_2$ is a straight or branched chain saturated aliphatic hydrocarbon group and the total number of carbon atoms in $R_1$ and $R_2$ is 12 to 18.

16. The emulsifier composition as claimed in claim 15, wherein the total number of carbon atoms in $R_1$ and $R_2$ in the formula (II) is 16.

17. The emulsifier composition as claimed in claim 15 or 16 wherein $R_1$ and $R_2$ in the formula (II) are each a branched saturated aliphatic hydrocarbon group.

18. The emulsifier composition as claimed in claim 12 wherein R is a 5,7,7-trimethyl-2-(1,3,3-trimethylbutyl)-octyl group.

19. The emulsifier composition as claimed in claim 15 or 16 wherein $R_1$ and $R_2$ in the formula (II) are each a straight chain saturated aliphatic hydrocarbon group.

20. The emulsifier composition as claimed in claim 12 wherein R is a 2-heptyl undecyl group.

* * * * *